(12) United States Patent
Leddy et al.

(10) Patent No.: US 8,080,206 B2
(45) Date of Patent: Dec. 20, 2011

(54) MULTICOMPONENT ANALYSIS OF VOLATILE ORGANIC COMPOSITIONS IN VAPOR SAMPLES

(75) Inventors: Johna Leddy, Iowa City, IA (US); Luke M. Haverhals, Coralville, IA (US)

(73) Assignee: The University of Iowa Research Foundation, Iowa City, IA (US)

( * ) Notice: Subject to any disclaimer, the term of this patent is extended or adjusted under 35 U.S.C. 154(b) by 1546 days.

(21) Appl. No.: 11/090,318

(22) Filed: Mar. 25, 2005

(65) Prior Publication Data

US 2005/0214169 A1  Sep. 29, 2005

Related U.S. Application Data

(60) Provisional application No. 60/556,975, filed on Mar. 26, 2004.

(51) Int. Cl.
*G01N 33/48* (2006.01)
(52) U.S. Cl. .............................. 422/83; 422/80; 429/400
(58) Field of Classification Search .................... 422/80, 422/83; 429/400
See application file for complete search history.

(56) References Cited

U.S. PATENT DOCUMENTS

| | | | |
|---|---|---|---|
| 3,966,579 A | 6/1976 | Chang et al. |
| 4,487,055 A | 12/1984 | Wolf |
| 4,749,553 A | 6/1988 | Lopez et al. |
| 4,770,026 A | 9/1988 | Wolf |
| 4,926,164 A | 5/1990 | Porter et al. |
| 5,048,321 A | 9/1991 | Chow |
| 5,081,871 A | 1/1992 | Glaser |
| 5,132,193 A | 7/1992 | Reddy et al. |
| 5,291,898 A | 3/1994 | Wolf |
| 5,302,471 A | 4/1994 | Ito et al. |
| 5,426,415 A | 6/1995 | Prachar et al. |
| 5,458,853 A | 10/1995 | Porter et al. |
| 5,595,832 A | 1/1997 | Tomimatsu et al. |
| 5,595,833 A | 1/1997 | Gardner et al. |
| 5,753,185 A | 5/1998 | Mathews et al. |

(Continued)

FOREIGN PATENT DOCUMENTS

WO  WO 92/22813  12/1992

(Continued)

OTHER PUBLICATIONS

Freudernrich, How Breathalyzers Work, www.howstuffworks.com, 1998-2007, 4 pages.

(Continued)

*Primary Examiner* — Lyle Alexander
(74) *Attorney, Agent, or Firm* — Foley & Lardner LLP (57) ABSTRACT

Amounts of volatile organic compositions can be evaluated from vapor samples based on the time dependent response of a fuel cell contacted with the vapor sample at its anode. The time response of the fuel cell signal, e.g., voltage or current, is de-convoluted using a set of standard curves for an equivalent fuel cell configuration obtained separately for each of the volatile organic compositions of a fuel cell with an equivalent construction as the sample-evaluation fuel cell. The methodology can be implemented on a system with an appropriate vapor collection device suitable for the particular application. The method and system can be used to analyze breath samples to evaluate ethanol levels or other volatile organic composition. The system can be a breathalyzer, a vehicle interlock, a medical analysis device or a sensor of environmental or industrial interest.

9 Claims, 8 Drawing Sheets

U.S. PATENT DOCUMENTS

| | | | |
|---|---|---|---|
| 5,928,804 A | 7/1999 | Leddy et al. | |
| 6,479,176 B2 | 11/2002 | Leddy et al. | |
| 6,726,636 B2 * | 4/2004 | Der Ghazarian et al. | 600/532 |
| 6,795,775 B2 | 9/2004 | Traylor, III | |
| 6,893,756 B2 * | 5/2005 | Clingerman et al. | 429/22 |
| 7,421,882 B2 | 9/2008 | Leddy et al. | |
| 2002/0084130 A1 | 7/2002 | Der Ghazarian et al. | |
| 2002/0149466 A1 * | 10/2002 | Sunshine et al. | 338/34 |
| 2002/0177232 A1 | 11/2002 | Melker et al. | |
| 2002/0198574 A1 | 12/2002 | Gumpert | |
| 2003/0004426 A1 | 1/2003 | Melker et al. | |
| 2003/0117287 A1 | 6/2003 | Crespo | |
| 2003/0121309 A1 | 7/2003 | Fikus et al. | |
| 2003/0183437 A1 * | 10/2003 | Mendoza | 180/272 |
| 2003/0208133 A1 | 11/2003 | Mault | |
| 2004/0101741 A1 * | 5/2004 | Minteer et al. | 429/43 |
| 2004/0137637 A1 | 7/2004 | Wang et al. | |
| 2004/0236244 A1 * | 11/2004 | Allen et al. | 600/532 |
| 2005/0084921 A1 | 4/2005 | Cranley et al. | |
| 2005/0214169 A1 | 9/2005 | Leddy et al. | |
| 2006/0130557 A1 | 6/2006 | Leddy et al. | |

FOREIGN PATENT DOCUMENTS

| | | |
|---|---|---|
| WO | WO 93/05393 | 3/1993 |
| WO | WO 93/05393 A | 3/1993 |

OTHER PUBLICATIONS

Alcohol and the Human Body, Intoximeters, Inc., 1995-2007, 6 pages.

Harris et al., Self Monitoring of Blood Glucose by Adults With Diabetes in the United States, Diabetes Care, Aug. 1993, vol. 16, No. 8, pp. 1116-1123, 8 pages.

Tassopoulos et al., Breath-Acetone and Blood-Sugar Measurements in Diabetes, The Lancet, Jun. 28, 1969, vol. 1, pp. 1281-1286, 5 pages.

Musa-Veloso et al., "Breath Acetone is a Reliable Indicator of Ketosis in Adults Consuming Ketogenic Meals," American Journal of Clinical Nutrition, 2002, pp. 65-70, vol. 76.

Likhodii et al., "Breath Acetone as a Measure of Systemic Ketosis Assessed in a Rat Model of the Ketogenic Diet," Clinical Chemistry, 2002, pp. 115-20, vol. 48.

Fleischer et al., "Detection of Volatile Compounds Correlated to Human Diseases through Breath Analysis with Chemical Sensors," Sensors and Actuators B, 2002, pp. 245-249, vol. 83.

Musa-Veloso et al., "Epilepsy and the Ketogenic Diet: Assessment of Ketosis in Children Using Breath Acetone," Pediatric Research, 2002, pp. 443-448, vol. 52.

Phillips et al., "Variation in Volatile Organic Compounds in the Breath of Normal Humans," J. Chromatography B, 1999, pp. 75-88, vol. 729.

Phillips, "Method for the Collection and Assay of Volatile Organic Compounds in Breath," Analytical Biochemistry, 1997, pp. 272-278, vol. 247.

Yu et al., "Analysis of Diabetic Patient's Breathe Using Conducting Polymer Sensor Array," Chemical Sensors (2005), 305-308.

Phillips, "Detection of carbon disulfide in breath and air: a possible new risk factor for coronary artery disease," International Archives of Occupational and Environmental Health, 1992, pp. 119-123, vol. 64.

Phillips et al., "Volatile Organic Compounds in Breath as Markers of Lung Cancer: A Cross-Sectional Study," Lancet, 1999, pp. 1930-33, vol. 353.

Zhang et al., "Diagnosis of Diabetes by Image Detection of Breath using Gas-Sensitive Laps," Biosensors & Bioelectronics, 2000, pp. 249-256, vol. 15.

Wang et al., "Blood Acetone Concentration in 'Normal People' and in exposed workers 16 h after the end of the workshift," International Achieves of Occupational and Environmental Health, 1994, pp. 285-89, vol. 65.

Kalapos, "On the Mammalian Acetone Metabolism: From Chemistry to Clinical Implications," Biochimica et Biophysica Acta, 2003, pp. 122-139, vol. 1621.

Diskin et al., "Increase of Acetone and Ammonia in Urine Headspace and Breath During Ovulation Quantified using Selected Ion Flow Tube Mass Spectrometry," Institute of Physics Publishing; Physiol. Meas., 2003, pp. 191-199, vol. 23.

Goschke et al., "Aceton in der Atemluft and Ketone im Venenblut bei vollständigem Fasten normal-und übergewichtiger Personen," Res. Exp. Med., 1975, pp. 233-244, vol. 165.

Sacks et al., "Guidelines and Recommendations for Laboratory Analysis in the Diagnosis and Management of Diabetes Mellitus," Chemical Chemistry, 2002, pp. 436-72, 48:3.

Laffel, "Ketone Bodies: A Review of Physiology, Pathophysiology and Application of Monitoring to Diabetes," Diabetes/Metabolism Research and Reviews, 1999, pp. 412-426, vol. 15.

Kim et al., Sensors and Actuators B, 2000, vol. 67, p. 194-198.

Fenske et al., J. Air Waste Management Assoc., May 1999, vol. 49, p. 594-598.

Glover, "Toluene and the Intoxilyzer 5000: No response to concentrations found on human breath" International Conference on Alcohol, Drugs and Traffic Safety, May 22-26, 2000.

Jones, "Fifty years on-looking back at developments in methods of blood- and breath alcohol analysis," International Conference on Alcohol, Drugs and Traffic Safety, May 22-26, 2000.

Manolis, "The Diagnostic Potential of Breath Analysis," Clin. Chem., vol. 29, No. 1, 1983, pp. 5-15.

Millet et al., J. Applied Electrochem., 1996, vol. 26, p. 933-937.

Pausson et al., Forensic Science International, 1999, vol. 105, p. 95-114.

Sanchez et al., Anal. Chem., May 15, 2003, vol. 75, p. 2231-2236.

Verstraete, "Perspectives for the detection of cannabis in breath" International Conference on Alcohol, Drugs and Traffic Safety, May 22-26, 2000.

PCT/US2005/010118 filed Mar. 25, 2005, Intl. Prel. Report on Patentability and Search Report dated May 4, 2007 (7 pages).

U.S. Appl. No. 12/192,038, filed Aug. 14, 2008, Leddy et al.
U.S. Appl. No. 12/192,050, filed Aug. 14, 2008, Leddy et al.
U.S. Appl. No. 12/192,056, filed Aug. 14, 2008, Leddy et al.

* cited by examiner

MULTICOMPONENT ANALYSIS OF VOLATILE ORGANIC COMPOSITIONS IN VAPOR SAMPLES

CROSS REFERENCE TO RELATED APPLICATIONS

This application claims priority to copending U.S. Patent Application Ser. No. 60/556,975 filed on Mar. 26, 2004 to Leddy et al., entitled "Multicomponent Analysis of Human Breath Using Fuel Cells As Sensors," incorporated herein by reference.

FIELD OF THE INVENTION

The invention relates to approaches for measuring and differentiating volatile organic compositions in vapor samples, such as human breath. In particular, the invention relates to the use of fuel cells as sensors for volatile organic compositions.

BACKGROUND OF THE INVENTION

More than 200 organic compounds have been detected in breath exhaled from humans. Volatile Organic Compounds (VOCs) such as alcohols, aldehydes, hydrocarbons, and ketones are constituents of human breath at parts per trillion (ppt) to parts per million (ppm) levels. For a more complete discussion of VOCs in human breath, see, for example, A. Manolis, Clin. Chem. 1983, Vol. 29, p 5; J. Fenske et al., J. Air Waste Management Assoc., 1999, Vol. 49, p. 594; and R. Sachs et al., Anal. Chem. 2003, Vol. 75, p 2231, all three of which are incorporated herein by reference. The concentrations of VOCs in breath are representative of their concentrations in blood through rapid gas exchange at the blood/gas interface in the lungs. By analyzing human breath, one can probe the general health of an individual and uncover exposure(s) to drugs or environmental pollutants. Both volatile organic compounds, such as solvents, can be of concern in environmental and industrial contexts.

Very few VOCs in breath are able to be measured (quantitatively or qualitatively) by methodologies suitable for routine evaluation. This is because most VOCs in breath are present at very low concentrations so that preconcentration techniques coupled with complicated separation and detection methods, such as gas chromatography and mass spectrometry, generally would be used to determine their presence. This type of breath analysis methodology requires technical skill, is expensive, and is generally not portable so that it is not practically employed in the field. One notable exception is the determination of Blood Alcohol Concentration or Blood Alcohol Content (BAC) by breath analysis for the VOC analyte ethanol.

Ethanol is a by-product of respiration and is found to be in human breath whether or not an individual has been consuming it. Elevated levels of ethanol necessary for behavioral impairment, in most circumstances, is only possible by ingestion and is a matter of law. BAC is a measurement of the mass of alcohol (ethanol) in a given volume of blood, mg (milligrams) ethanol per 100 ml (milliliters) blood. For instance, 0.04 BAC implies a concentration of 40 mg of alcohol in 100 mL (milliliters) of blood In the U.S., BrAC is specified as BAC/2100. Ethanol at 34° C. is in equilibrium at blood at a ratio of roughly 2100:1 based on the distribution of alcohol in equilibrium with the blood in the deep part of the lungs. In other words, 2100 ml of air in the deep parts of the lungs contain the same amount of alcohol that is present in 1 ml of blood Indirectly measuring BAC through breath analysis (BrAC) can be accomplished by infrared spectroscopy (IR), chemical reactions to produce color changes, semiconductor sensors, and fuel cells (FCs). See, for example, further discussion of these approaches in Choi et al., Sensors and Actuators B, 2000, Vol 67, p 194; P. Millet et al., J. Applied Electrochem., 1996, Vol. 26, p 933; A. Jones, "Fifty years on—looking back at developments in methods of blood- and breath alcohol analysis," International Conference on Alcohol, Drugs and Traffic Safety, May 22-26, 2000; and N. Pausson et al., Forensic Science International, 1999, Vol. 105, p 95, all four of which are incorporated herein by reference.

Sensitivity and selectivity to ethanol vary for all BrAC methodologies mentioned above. In addition, BrAC measurements are subject to variability due to the difficulties in obtaining consistent breath samples. Infrared spectroscopy and FCs are utilized extensively, either alone or in tandem, in evidentiary BrAC measuring instruments. At present, fuel cells are the sensor technology of choice in portable BrAC measurement instruments, mainly due to the physical constraints on hardware design. Two examples of portable BrAC measurement instruments are field sobriety measurement devices used by law enforcement and interlocks used to prevent repeat offenders of driving while intoxicated from starting their vehicle if they have a BrAC over a selected value.

SUMMARY OF THE INVENTION

In a first aspect, the invention pertains to a method for evaluating amounts of a plurality of volatile compositions in a vapor sample. Suitable volatile compositions can be particular organic compounds, or other compositions, such as mixtures of compounds. The method comprises fitting a time response curve of a sample-evaluation fuel cell in which the fuel cell anode is contacted with the vapor sample. The analysis is based on a function of standard time response curves for an equivalent fuel cell configuration obtained separately for each of the volatile organic compositions on a fuel cell with equivalent construction as sample-evaluation fuel cell. The method can be used to obtain alcohol levels from a breath sample. In particular, the methods measure components on the breath of smokers or other individuals with a mixture of significant analytes in the breath. Thus, the approach can discriminate and quantify the individual compositions associated with alcohol consumption and smoking. In other embodiments, the method can be used to evaluate the health of an individual. The method can be used to control a vehicle interlock. Also, gaseous samples of environmental and industrial import can be examined.

In a further aspect, the invention pertains to a system comprising a sample collector, a flow apparatus, a fuel cell and an analyzer. The flow apparatus is configured to receive a sample from the sample collector. The fuel cell comprises an anode connected to the flow system such that the sample transported within the flow system contacts the anode. Furthermore, the analyzer receives a signal related to the voltage/potential or current from the fuel cell, and evaluates the amounts of a plurality of volatile organic compositions from the time response of the fuel cell signal as a function of time. The evaluation is performed through a de-convolution of the time response of the fuel cell based on separate standard time response functions from each of the volatile organic compositions. The system can be a portable unit, i.e., the unit can be easily ambulatory with an average individual. In other embodiments, the system is operably connected to a vehicle interlock.

DETAILED DESCRIPTION OF THE INVENTION

The signature of the time response curve for a fuel cell signal, e.g., voltage/potential or current, upon exposure with volatile organic compositions from a breath sample can be used to evaluate the relative concentrations of a combination of compositions in the sample. Corresponding systems are designed to collect a vapor sample that contains volatile compositions and direct the sample to the anode of a fuel cell. The fuel cell response as a function of time is a signature for a particular compound. For samples that have a plurality of volatile organic compositions, the fuel cell response is for practical purposes a linear or nonlinear combination of the response of the fuel cell for the particular compositions appropriately weighed for the relative amounts. Therefore, an analysis can be performed to de-convolute the time response curve to obtain values for the relative concentrations. Average standard curves can be used for the performance of the de-convolution. In some embodiments, the vapor sample is a breath sample from a person, or other patient, such as a pet or farm animal for medical evaluation.

Generally, a volatile organic composition evaluation system comprises a vapor/gas sampling component, a flow apparatus, a fuel cell and an analysis instrument. Vapor refers generally to gas(es) and/or vapor of a volatile composition(s) at a particular vapor pressure. The sampling component comprises an appropriate collection system suitable for the particular application of the system. For a breath analyzer, the sampling component can comprise a mouthpiece and associated conduits to connect the flow with the flow apparatus. The flow apparatus directs the gas sample to a fuel cell. The fuel cell comprises an anode operably connected to the flow apparatus in which the fuel cell generates a voltage in response to a broad range of volatile organic compositions reacting at the anode. The analysis instrument measures the fuel cell output signal, e.g., voltage or current, as a function of time from the fuel cell and evaluates the composition of the vapor in response to the fuel cell performance as a function of time.

Fuel cells of particular interest are proton exchange membrane fuel cells, also known as PEM fuel cells. Polymer electrolyte membrane fuel cells are one type of proton exchange membrane fuel cells. Proton exchange membrane fuel cells have a separator or electrolyte between the anode and cathode that provides for transport of protons across the separator. Generally, the separator/electrolyte is hydrated to perform its function as electrolyte. The separator can be a polymer film. PEM fuel cells operate at lower temperatures than most other fuel cell types with operating temperatures generally less than about 100° C. and can be operated at temperatures down to freezing.

Other types of fuel cells may also be appropriate, such as phosphoric acid fuel cells, molten carbonate fuel cells and solid oxide fuel cells. Phosphoric acid fuel cells use phosphoric acid as the electrolyte. These fuel cells generally operate at about 150° C. to about 220° C. The electrolyte for molten carbonate fuel cells is molten carbonate salts, as their name implies. To achieve sufficient ion mobility through the carbonate salts, these fuel cells operate at temperatures on the order of 650° C. The electrolyte for solid oxide fuel cells is a ceramic oxide material that can transport $O^{2-}$ ions at temperatures from 600° C. to about 1000° C. Phosphoric acid fuel cells, molten carbonate fuel cells and solid oxide fuel cells are described, respectively, in U.S. Pat. No. 5,302,471 to Ito et al., entitled "Compact Phosphoric Acid Fuel Cell System And Operating Method Thereof," U.S. Pat. No. 5,595,832 to Tomimatsu et al., entitled "Molten Carbonate Fuel Cell," and U.S. Pat. No. 5,595,833 to Gardner et al., entitled "Solid Oxide Fuel Cell Stack," all of which are hereby incorporated by reference herein. Since PEM fuel cells are desired due to their operating temperatures and other desirable characteristics, the following discussion focuses on these embodiments, although other fuel cell types can be substituted based on the disclosure herein.

Suitable PEM fuel cells generally are not optimized for performance with a particular fuel. Thus, the fuel cell should have an appropriate response for a range of organic and/or inorganic fuels. While commercial fuel cells for ethanol detection may not be well suited for the present applications, they can provide acceptable performance for the present applications. PEM fuel cells generally have catalyst materials in contact with both sides of the electrolyte/separator. One side forms the cathode where oxygen or other oxydizing agent is reduced. The other side of the electrolyte/separator forms the anode where the composition is oxidized. Protons flow from the anode to the cathode as mediated by the electrolyte.

In some embodiments, fuel cells with magnetic composites can be particularly desirable due to their improved transport of paramagnetic materials, such as oxygen to the cathode. Fuel cells with magnetic materials incorporated into the fuel cell are described further, for example, in U.S. Pat. No. 6,479,176 to Leddy et al, entitled "Gradient Interface Magnetic Composites And Methods Therefor," and U.S. Pat. No. 5,928,804 to Leddy et al., entitled "Fuel Cells Incorporating Magnetic Composites Having Distinct Flux Properties," both of which are incorporated herein by reference.

For power production, fuel cells are generally formed into stacks with a series of fuel cells connected in series to generate an additive voltage from the cells. Bipolar plates or other suitable current collector with flow channels separate adjacent cells. However, in general, for the present application, a single fuel cell of modest size is suitable that generates a reasonable voltage for the particular supply of volatile organic compositions. Using a single fuel cell, the structure of the systems can be much simpler in comparison with a fuel cell stack, especially with respect to the flow of fuel and oxidizing agent, generally, oxygen from air.

The analysis is based on a unique time dependent signature of the different volatile organic compositions with respect to the time dependent response of a fuel cell operating using the volatile organic composition as the fuel. To de-convolute the time dependent response curve, standard curves are generated for selected volatile organic compounds or particular mixtures thereof, which are thought or known to be in a sample for analysis. The particular mixtures can be analyzed together as a particular composition. For example, tobacco smoke, such as cigarette smoke, has a mixture of volatile organic compounds that are relatively fixed with respect to relative amounts such that the mixture can be considered a separate composition that is analyzed together for the purposes of the de-convolution. The standard curves can be based on averages from a plurality of runs to improve the precision and accuracy of the standard curve. Then, the sample curve can be de-convoluted with the standard curves. The de-convolution can be based on a linear or non-linear combination at a plurality of time points.

The methodologies described herein can be used in a variety of applications, such as breathalyzers, vehicle interlocks, medical diagnostics, and environmental evaluations. Fuel cells are already used commercially for breathalyzers for the detection of ethanol to determine if the values are within legal limits. Portable devices can be used by law enforcement officials for testing drivers suspected of driving under the influence of alcohol. Similarly, other devices have been connected to vehicles, especially automobiles, for the evaluation of the sobriety of a potential driver and disabling the vehicle as appropriate. These devices can benefit from the improved analytical systems and methodologies described herein since more accurate readings can be obtained if a variety of sources of volatile organic compositions can be distinguished. In other embodiments, measurements from the systems described herein can assist with medical evaluations since the presence of certain compositions in the breath can be indicative of certain illnesses or conditions. Furthermore, volatile compositions, e.g., organic solvents and the like, are often environmental pollutants that result from a wide range of human activities. The ability to efficiently identify pollutants in a particular gas sample can greatly facilitate the evaluation of a potential environmental pollutant. Similar to the evaluation of environmental pollutants, analyses can be performed in industrial settings to evaluate release of pollutants and/or to evaluate exposure levels to individuals to determine if they are within acceptable levels. These industrial limits may be evaluated in view of specific regulations, such as regulations from the U.S. Occupational Health and Safety Administration (OSHA) or the U.S. Environmental Protection Agency (EPA).

Vapor Analysis System

A vapor analysis system generally comprises a vapor/gas sampling component, a flow apparatus, a fuel cell and an analysis instrument. The sampling component can be designed based on the source of the particular sample. In some embodiments of interest, the vapor sampling component can be a breath collection component. The flow apparatus provides for controlled flow of the vapor sample to the fuel cell. The analysis instrument collects the time dependent response of the fuel cell following interaction with the vapor sample and the de-convolution of the time dependent response of the fuel cell to obtain the relative amounts of the samples. While the fuel cell can be optimized for certain analytes, general fuel cells can be used that are responsive to organic compositions and/or inorganic compositions generally.

Figure 1:
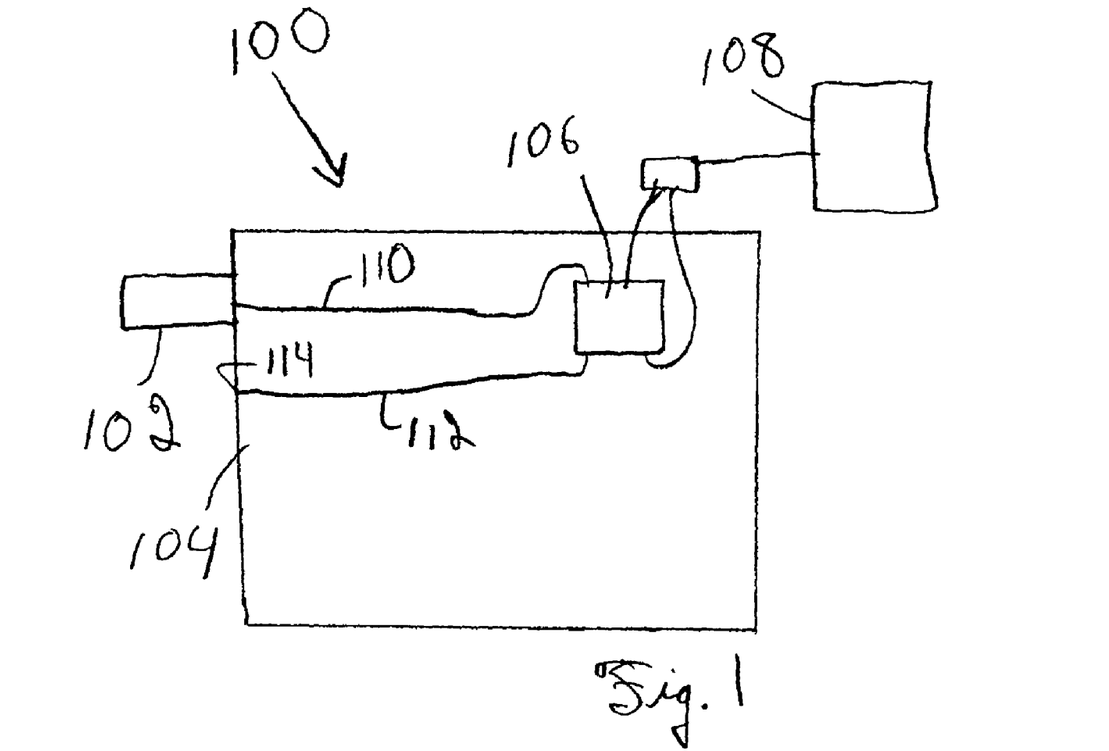
FIG. 1 is a schematic representation of a system for evaluation of amounts of volatile organic compositions in a vapor sample as described herein.

Referring to FIG. 1, a schematic is shown for a vapor analysis system described herein. As depicted in FIG. 1, vapor analysis system 100 can comprise sampling component 102, flow apparatus 104, fuel cell 106 and analysis instrument 108. Sampling component 102, which facilitates introducing a vapor sample into flow apparatus 104. In general, sampling component 102 can be any mechanical or passive structure that facilitates collection and introduction of desired vapors into the flow apparatus and/or the fuel cell of a vapor analysis system. Sampling component 102 can comprise appropriate combinations of one or more tubes, mouthpieces, or the like.

In some embodiments, flow apparatus 104 can comprise inlet flow line 110, which provides a fluid flow pathway for vapor samples from sampling component 102 to the anode of fuel cell 106. Flow apparatus 104 can also comprise outlet flow line 112, which provides a vapor flow pathway for vapor samples and/or fuel cell by-products from the anode of fuel cell 106 to, for example, exhaust 114. In some embodiments, flow apparatus 104 and/or fuel cell 106 can comprise one or more pumps to facilitate moving vapor samples into and out of the anode of fuel cell 106. Vapor analysis system 100 can be configured to function in a variety of devices such as, for example, breathalyzers, ignition interlock systems, medical diagnostic devices, and environmental and industrial sensors or monitors.

As described below, the various components of vapor analysis system 100 can be adjusted and designed to suit the intended application of the device. In embodiments where the vapor analysis system is designed to be incorporated into a breathalyzer, sampling component 102 can comprise stem having a tube fitting adapted to removeably engage a sample tube or mouthpiece. In some embodiments, the stem can be formed integrally with the housing of the breathalyzer. Breathalyzers having a stem and a tube fitting are described in U.S. Pat. No. 4,487,055 to Wolf, entitled "Breath Alcohol Testing Device," which is hereby incorporated by reference herein. In embodiments where the vapor analysis system is designed to be incorporated into an ignition interlock, sampling component 102 can comprise a mouthpiece that extends from the interior of the housing to the exterior of the housing. Sampling components for ignition interlocks are described in, for example, U.S. Pat. No. 5,426,415 to Prachar et al., entitled "Breath Analyzer For Use In Automobile Ignition Locking Systems," which is hereby incorporated by reference herein. In other embodiments, the vapor analysis system can be incorporated in medical diagnostic devices or an environmental sensor or detector. Suitable breath sampling components for a medical examination are described, for example, in U.S. Pat. No. 5,081,871 to Glazer, entitled "Breath Sampler," incorporated herein by reference. Suitable environmental sampling systems is described for example in U.S. Pat. No. 5,753,185 to Mathews et al., entitled "Vehicle Emissions Testing System," incorporated herein by reference.

The vapor analysis devices 100 of the present disclosure can include a flow apparatus 104 that provides desired fluid flow within vapor analysis device. In general, flow apparatus 104 can regulate and provide fluid flow to and from fuel cell 106 during analysis of a sample. Flow apparatus can comprise appropriate combinations of flow lines or pipes and one or more pumps to facilitate desired fluid flow within vapor analysis system 100. The pump and/or other flow control elements can be connected to a microcomputer, which can control the function of the pump, and thus the introduction of vapor samples into fuel cell 106.

A flow apparatus suitable for use in ignition interlock systems is disclosed in, for example, U.S. Pat. No. 5,426,415 to Prachar et al., entitled "Breath Analyzer For Use In Automobile Ignition Locking Systems," which is hereby incorporated by reference herein. In this system, a diaphragm pump is used to divert a portion of a breath sample through a fuel cell anode while exhausting flow from the anode. Flow structures suitable for use in a breathalyzers are described in, for example, U.S. Pat. No. 4,487,055 to Wolf, entitled "Breath Alcohol Testing device," and in U.S. Pat. No. 5,291,898 to Wolf, entitled "Breath Alcohol Device," both of which are incorporated herein by reference. In these systems, a diaphragm draws breath into and from a chamber adjacent a fuel cell anode to control exposure of the fuel cell anode to the breath.

As described above, flow apparatus 104 can be connected to one or more fuel cells 106 to facilitate analysis of a vapor sample. Fuel cell 106 can be any fuel cell that can produce a response to desired compositions. Suitable fuel cells include, for example, PEM fuel cells, phosphoric acid fuel cells, molten carbonate fuel cells and solid oxide fuel cells, as noted above. In some embodiments, fuel cell 106 can be a PEM fuel cell comprising a proton exchange membrane as the electrolyte, such as Nafion®, with catalyst particles in contact with the electrolyte forming the anode and cathode. A current collector contacts the electrolyte particles to complete the electrodes. A particular embodiment is described further with respect to the Examples below. In some breathalyzer fuel cells, the separator is formed from sintered or pressed polymer balls, such as polyvinylchloride, to form pores with about 1 to about 25 micron diameters extending through the membrane. A layer of catalyst mixed with conductive carbon and binder is applied to each side of the membrane to form the anode and cathode. The porous framework is filled with sulfuric acid, phosphoric acid or a mixture thereof to complete the circuit.

Suitable analysis instruments include, for example, windows based computers, person digital assistants, and dedicated computer processors, i.e., microprocessor, integrated into a portable analysis apparatus, in which portable digital assistant technology can be incorporated into the apparatus.

Analysis Algorithm

The time dependent response of the fuel cell is dependent on the chemical composition of the fuel for vapor sampling systems, such as those described above. Thus, if a sample comprises a plurality of volatile organic compositions that can fuel the fuel cell, the time dependent response curve of the fuel cell reflects the overall composition of the vapor sample. The de-convolution of the time dependent response curve can be used then to obtain the amounts of the different volatile organic compositions in the vapor sample. The de-convolution can be based on a linear combination or a nonlinear combination of the independent response curves. The de-convolution of the vapor sample is based on standard curves for the individual compositions, which may be normalized.

To perform the analysis, each curve can be converted to a vector by the selection of a specific number of time points. The dimension of each vector, i.e., the number of time points used, can be selected to obtain a desired degree of fitting. The number of time points is selected to yield a desired accuracy of the de-convolution. All of the collected time points can be used in the analysis such that the hardware response time sets the spacing of the time points, although a subset of the time points can be used as desired. Generally, the data is collected until the signal has significantly decayed from its peak value, and in some embodiments the signal is monitored until it has decayed 60 percent from its peak value, in further embodiments 75 percent from its peak value and in additional embodiments 85 percent from its peak value. A person of ordinary skill in the art will recognize that additional ranges for the time cut-off within the explicit ranges are contemplated and are within the present disclosure.

Generally, the degree of fitting does not significantly increase after a certain number of time points are selected. The number of time points may be fixed by the timing of the data collection system and the response time for the analog-to-digital conversion. In general, the number of point can be from . . . . The time points do not necessarily have to be equally spaced, although certain spacings may be convenient for certain types of numerical analysis. The resulting vector can be written as V with elements $v_n$ for the nth time point recorded.

Each standard vector is normalized to a normalized vector NV for the later de-convolution. Specifically, the normalization is performed according to:

$$\text{The Nth Normalized element in } NV = Nv_n = (v_n - v_{small})/(v_{large} - v_{small}), \quad (1)$$

where $v_{small}$ is the smallest element in V, $v_{large}$ is the largest element in V. Equation (1) ensures that the largest value in NV is 1 and the smallest value is 0. Other normalizations can be used to standardize the peak value, if desired, although the normalization in Eq. (1) has been found in the examples below to yield good results.

A number of normalized curves from known samples can be averaged to get a standard curve for a particular analyte, such as ethanol, cigarette smoke, other tobacco smoke or any other volatile organic composition. The standard vector for analyte "a" from an average of i sample runs can be written as:

$$\text{Nth element of the standard vector for analyte } a = v_{na} = (Nv_{na1} + Nv_{na2} + \ldots + Nv_{nai})/i, \quad (2)$$

where $Nv_{nai}$ is the nth normalized element at $t_n$ for the ith sample of analyte a. Slight variations between vectors $NV_1$ to $NV_i$ distort the values of $V_{average}$, so that the largest value in $V_{average}$ is not necessarily equal to 1, and the smallest value in $V_{average}$ is not necessarily equal to 0. Thus, the average response curve itself can be normalized based on the formula in Eq. 1 to obtain a normalized average or standard curve for a particular analyte, $NV_{average}$.

A linear combination of the vectors $NV_{average,A}$, $NV_{average,B}$, $NV_{average,C}$, etc. can be used to form a vector V that approximates a sample vector. In principle, any number of standard vectors for analytes A, B, C, D, . . . can be used. In some embodiments, there are 2 analytes, such as ethanol and cigarette smoke, in other embodiments, 3 analytes, in further embodiments 4, in additional embodiments 50 or more, and any number in between. For two analytes, the equation is as follows:

$$V_{Lin.\ Combo.} = A \times NV_{average,A} + (1-A) \times NV_{average,B}, \text{ where } 0 \leq A \leq 1. \quad (3)$$

For three analytes A, B and C, this equation becomes, $$V_{Lin.\ Combo.} = A \times NV_{average,A} + B \times NV_{average,B} + (1-A-B) \times NV_{average,C}, \quad (4)$$

where $0 \leq A \leq 1$ and $0 \leq B \leq 1$. Equations for other numbers of analytes can be written based on these examples. In general, there are N−1 unknowns for N analytes. Thus, as long as there are at least N−1 time points, the linear combination (or nonlinear combination) can be fit, although having additional time points presumably leads to a better fit through an over determination of the linear fit.

The new linear combination vector can be normalized according to Eq. 1. Similarly, the sample vector can also be normalized to yield a vector $NV_{unknown}$. Because the two vectors, $NV_{Lin.Combo.}$ and $NV_{unknown}$ are normalized to the same range, the proportions of the signal due to the two analytes, ethanol and cigarette smoke in the example below, the proportions of the two analytes can be evaluated regardless of the absolute magnitude of the response. The calculation at some point involves scaling the linear combination curve to the actual measurement to obtain the absolute quantities of the analyte. This scaling back to the total values can be performed before or after the fitting.

The best fit for the unknowns can be determined using established mathematical techniques. Thus, for Eq. 3, $A_{BestFit}$ is determined, and similarly, for Eq. 4, $A_{BetFit}$ and $B_{BestFit}$ can be determined. For example, the unknown parameters can be obtained by iteration. The sum of the differences between the elements in $NV_{Lin.\ Combo.}$ and $NV_{Unknown}$ can be called the "Gross Error" and is defined by the following equation:

$$\text{Gross Error} = \Sigma |Nv_{n,unknown} - Nv_{n,Lin.\ Combo.}|, \quad (5)$$

Equation (5) results in a fit that weights all time points equally. Other expressions for the gross error can be used, if desired. This fitting to reduce the gross error to obtain the best fit can use standard approaches to automate the process. An initial value can be estimated for the parameters based on known information about the sample. Standard method for performing the fit are known, such as the Downhill Simplex Method and the Conjugate Gradient Method. These are described further, for example, in Numerical Recipes: The Art of Scientific Computing, W. H. Press et al., (Cambridge University Press, 1986), incorporated herein by reference.

Once the value of $A_{BestFit}$ is known, it can be used to obtain BrAC or other concentrations for other analytes besides ethanol. Similarly, if additional unknown parameters are calculated for other analytes, these can be used to obtain useful concentration information. For a particular parameter, the concentration data can be obtained from the following calculation:

$$\text{BrAC or other Concentration value} = A_{BestFit} \times C_{Calibration} \times (V_{large,LinCombo} - V_{small,LinCombo}) \times (V_{large,Unknown} - V_{small,Unknown}) \quad (6).$$

$C_{calibration}$ can be obtained from a calculation of the responses of a fuel cell to a known, pure analyte sample. The concentration value for the vapor sample is then divided by the response to yield $C_{Calibration}$. The last part of Eq. (6), i.e., $(V_{large,LinCombo} - V_{small,LinCombo}) \times (V_{large,Unknown} - V_{small,Unknown})$, uses the largest and smallest values in vectors $V_{Unknown}$ and $V_{LinCombo}$ and is a scalar ratio between the range of the response to the unknown sample and the range of the linear combination fit. Since the linear combination of the normalized analytes responses are used, this scalar ratio can be used to find the actual response curve for that analyte.

Equations (3) and (4) above are directed to linear combinations of the fuel cell response for the different analytes. However, there may be circumstances in which the analytes interact in the anode such that the response of the fuel cell may be non-linear with respect to the presence of the different analytes. For example, Eq. (3) can be generalized to:

$$V_{Nlin.\ Combo.} = A \times NV_{average,A} + (1-A) \times NV_{average,B} + C \times (NV_{average,A} \times NV_{average,B}). \quad (7)$$

The parameters for the nonlinear fit can be established by obtaining the smallest value of the Gross Error in a similar fashion as the linear parameters were established. The parameters A and (1−A) can similarly be used to evaluate concentrations of the analytes as described above.

EXAMPLES

The fuel cell test devices used in the following Examples were constructed by Consumer Safety Technology (CST) of Des Moines, Iowa. CST produces commercial breath analyzers for automobile ignition locking systems that prevent intoxicated individuals from driving. Examples of their interlock systems are described further, for example, in U.S. Pat. No. 5,462,415 to Prachar et al., entitled "Breath Analyzer For Use In Automobile Ignition Locking Systems," which is hereby incorporated by reference herein. In performing the measurements herein, the apparatus incorporated a design with a fuel cell as described below. The fuel cell is placed within the apparatus to provide regulated breath flow to the anode of the fuel cell. The fuel cell output voltage was converted to a digital signal with an A/D converter for analysis by a computer. The analysis was performed through an iteration using 0.001 increments in the parameters over the range of possible values. This approach is straightforward to implement with computationally limited processors.

The fuel cells used in the test devices are essentially described in U.S. Pat. No. 5,928,804 to Leddy et al., entitled, "Fuel Cells Incorporating Magnetic Composites Having Distinct Flux Properties," which is hereby incorporated by reference, except that the fuel cells did not contain magnetic composites. These fuel cells are proton exchange membrane fuel cells with Nafion® perfluoronated, sulfonic acid polymer used as the electrolyte/separator. The ionomer Nafion® has superior ionic conductivity. Platinum coated carbon black particles (20 weight percent platinum) were used as the catalysts the catalyst particles are formed by mixing Pt from Alfa Aesar with carbon black (XC-72 from E-Tek) and mixing vigorously with a drill. The fuel cells were prepared with catalytic ink preparation and application procedures, Nafion® membrane pretreatments, and hot press lamination techniques. Specifically, a catalytic ink is mixed from platinum, carbon black, water, ethanol and isopropyl alcohol. This combination is mixed thoroughly. This solution is applied to carbon cloth or carbon paper (Toray paper) by painting with a brush or spraying with an air brush. Suitable carbon paper or carbon cloth are avialable from Aldrich Chemical or E-Tek. Solubilized Nafion® (Ion Power or Aldrich) is then sprayed over the dry ink that has already been supplied to the electrode(s). The anode and cathode are formed equivalently. A Nafion® membrane (Aldrich or Ion Power) is sandwiched between the two electrodes and hot pressed at about 130 degrees C. under about 0.1 metric tons per square centimeter. The membrane electrode assembly (MEA) is allowed to cool while under pressure. Once cool to about 50 degrees C., the MEA can be removed from the press for use.

The catalyst/separator interface has the bulk of the catalyst sites available to volatile organic compositions in the vapor sample, in comparison with commercial breathalyzer fuel cells. The fuel cells were circular with diameters of about 1.5 centimeters and are mounted in cartridges for easy exchange within the testing apparatus. Due to their construction and corresponding high general sensitivity, the fuel cells have unique time response curves with respect to volatile compositions of interest. In particular, commercial breathalyzer fuel cells tend to be much more sensitive to ethanol than to other types of volatile organics.

The test apparatus provided for the introduction of various breath samples under specified conditions into the fuel cell. Data was collected at 10 Hz, i.e., 10 points per second for 1 to 100 seconds for a total of 990 time points. The cut off for the time was not significant after 30 seconds. Some testing was performed with standard solutions, while other testing was performed with actual human breath samples. To produce a breath-based test sample, human subjects blew into the device for ten seconds. The first six seconds of the sample were allowed to bypass the fuel cell. The last four seconds of a run come from deeper within the subjects lungs. Thus, last four seconds of the breath is sampled for flow into the fuel cell. A pump with a valve system controls the flow to the fuel cell. A computer records the fuel cell voltage multiplied by 10,000 as a function of time. The fuel cell temperature was 25° C. for all samples. To control the conditions for the test, the tests were performing a in a controlled environment chamber.

Example 1

This example is directed to the evaluation of reproducibility of the time response curves for different fuel cells assembled as described herein.

Three fuel cell test devices were constructed as described above. "Breath" samples were produced and introduced into each of the fuel cell test devices. The "breath" samples were generated using a Toxitest Breath Alcohol Simulator containing a 0.05 BAC standard solution. The solution was formed with a mixture of ethanol and water to simulate a blood sample and heated to 37° C. to simulate body temperature. Breath was bubbled through the solution to simulate a breath sample. A known quantity of the "breath" sample was introduced into the fuel cell of each fuel cell test device.

Figure 2:
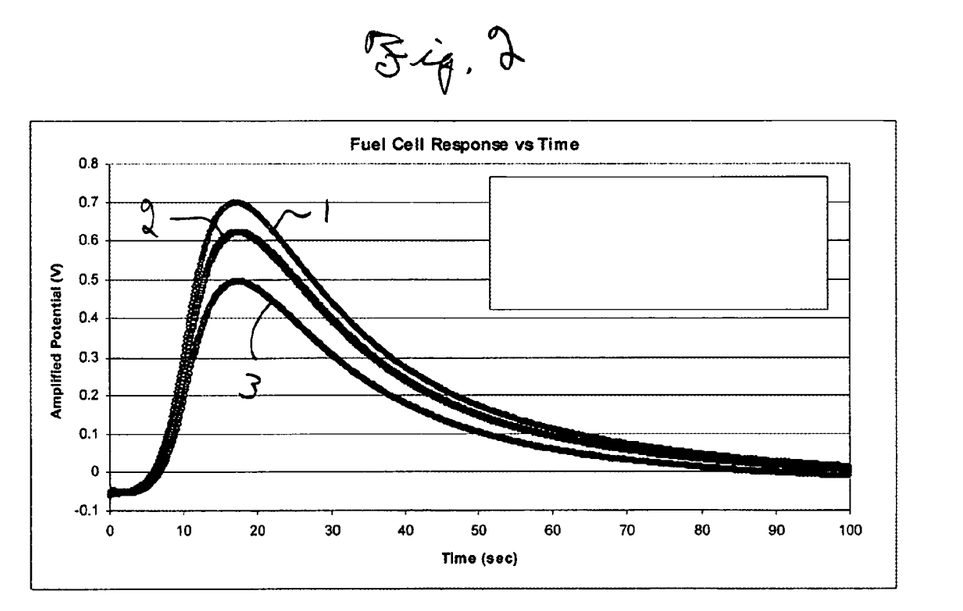
FIG. 2 is a plot of fuel cell response as a function of time for three fuel cells using a standard ethanol sample to compare the results of different fuel cells assembled into the apparatus for evaluating vapor samples.

As depicted in FIG. 2, the shape of the amplified potential v. time curve is similar for all three fuel cells. However, the magnitude of the three curves are different, with fuel cell 1 having the largest magnitude, followed by fuel cell 2 and fuel cell 3, respectively. The magnitude of each curve is different because of the inexact nature of catalyst application during construction. In other words, one particular fuel cell may have more catalyst than another fuel cell, which appears to affect the magnitude of the response curve but not the general shape of the response curve. Since the shapes of the curves are the same, the usefulness of the fuel cells for the detection of different volatile organic compositions should not depend on the magnitude of the available catalyst and differences in catalyst loading is at least in part corrected by the normalization.

Example 2

This example is directed to detection of cigarette smoke in breath as a function of time from inhaling smoke from the cigarette.

Figure 3:
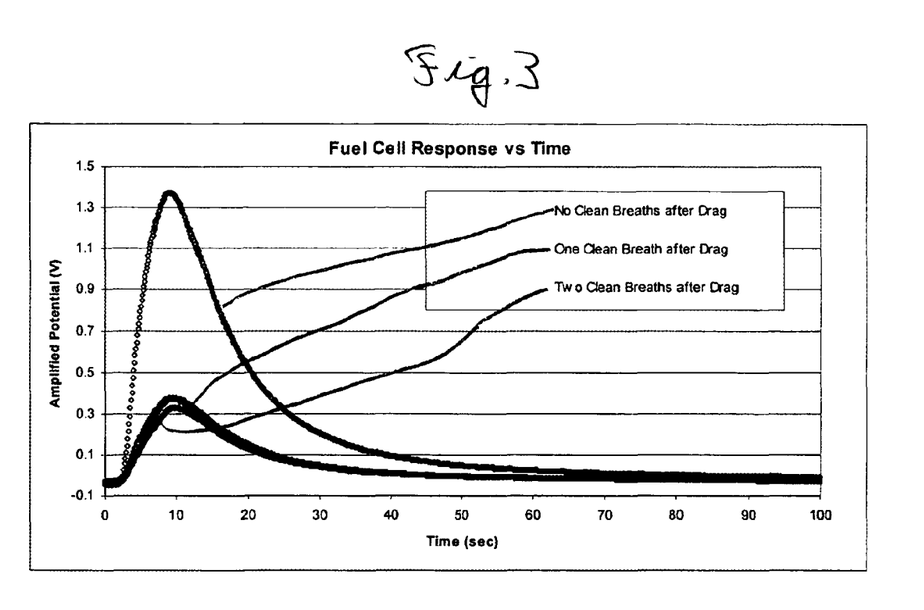
FIG. 3 is a plot of fuel cell response as a function of time for breath samples taken from a person after taking a drag on a cigarette, after taking one clean breath after a drag on a cigarette, and after two clean breaths following a drag on a cigarette.

Breath samples containing cigarette smoke from a single individual were introduced into a fuel cell test device as described above. The shape of the amplified potential v. time curve for each breath sample was similar, however, the magnitude of the curve decreased over time as the number of "clean" breaths after inhalation of the cigarette increased. In other words, the magnitude of the response to cigarette smoke is dependent on time. Referring to FIG. 3, the curve with the largest magnitude was from a breath sample taken after no clean breaths, while the curve with the smallest magnitude was from a breath sample taken after two clean breaths after a drag. The shape of the amplified potential v. time curve has been found to be consistent for at least one hour after a cigarette has been inhaled. Additionally, the shape of the curve has been consistent for different brands of cigarettes. Thus, the approaches described herein can be generally effective for the detection of cigarette smoke on human breath.

Example 3

This example is directed to the comparison of the breath of a non-smoker with the breath of a smoker after a 24 hour period without smoking.

Figure 4:
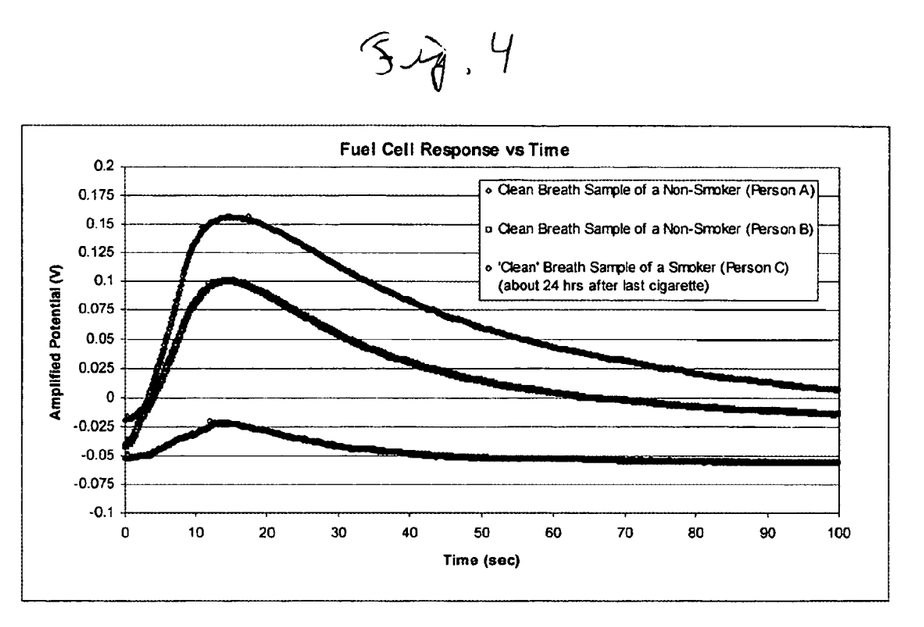
FIG. 4 is a plot of fuel cell response for the breath of two non-smokers and one smoker with at least 24 hours since having smoked their last cigarette.

Clean breath samples were introduced from different individuals into a fuel cell test device as described above. Two of the individuals who provided breath samples were non-smokers, while the other individual was a smoker who had not inhaled a cigarette for about 24 hours prior to giving the breath sample. As depicted in the FIG. 4, the shape of the amplified potential v. time curve for all three individuals is similar, and the magnitude of each response is small. Thus, significant voltage, or response, is not detected by individuals who have "clean" breath.

Example 4

This example demonstrates the ability to distinguish ethanol and cigarette smoke on the breath of a subject.

Breath samples from regular smokers who had been consuming alcohol were introduced into a fuel cell test device as described above. As depicted in the figures below, the total amplified potential v. time curve can be approximated as a linear combination of the separate responses to cigarette smoke and ethanol components based on the analysis using Equations (3) and (5) above. The linear combination fit was conducted for data taken between 1 and 100 seconds, using a data sampling rate of 10 Hz.

Figure 5:
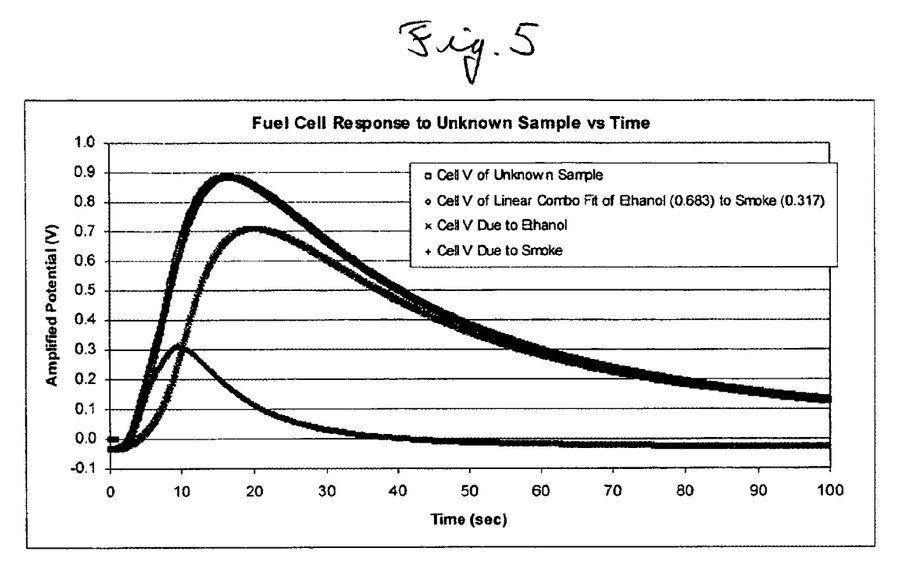
FIG. 5 is a plot of fuel cell as a function of time after an unknown sample from a smoker with ethanol on their breath, plotted along with a fit to ethanol and smoke from standard curves and the resulting curve fit to the unknown sample.
Figure 6:
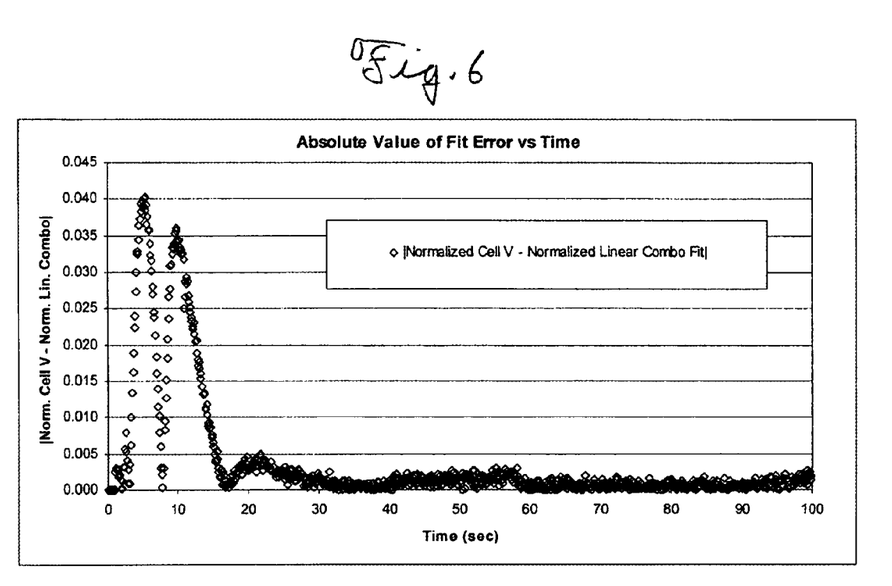
FIG. 6 is a plot of the absolute value of the unknown sample response minus the normalized recombination fit for the data in FIG. 5.
Figure 7:
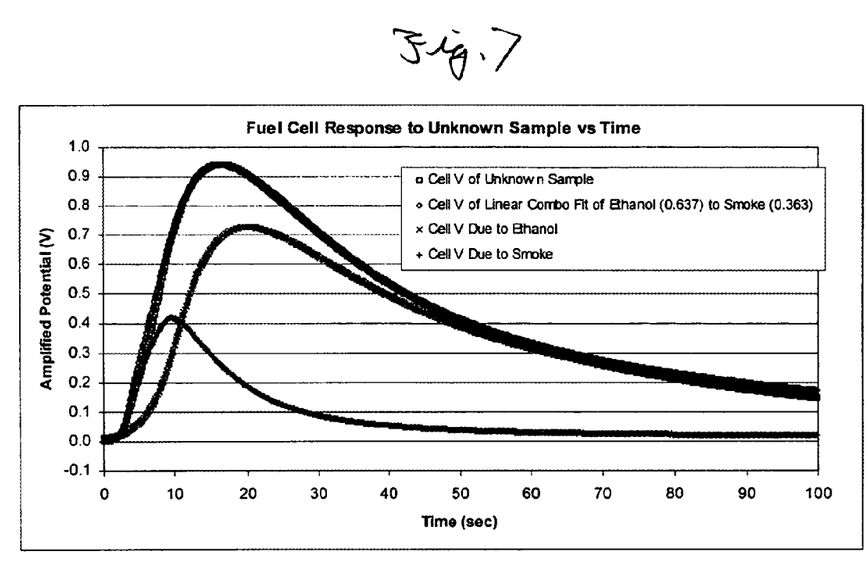
FIG. 7 is a plot of fuel cell as a function of time after a second unknown sample from a smoker with ethanol on their breath, plotted along with a fit to ethanol and smoke from standard curves and the resulting curve fit to the second unknown sample.
Figure 8:
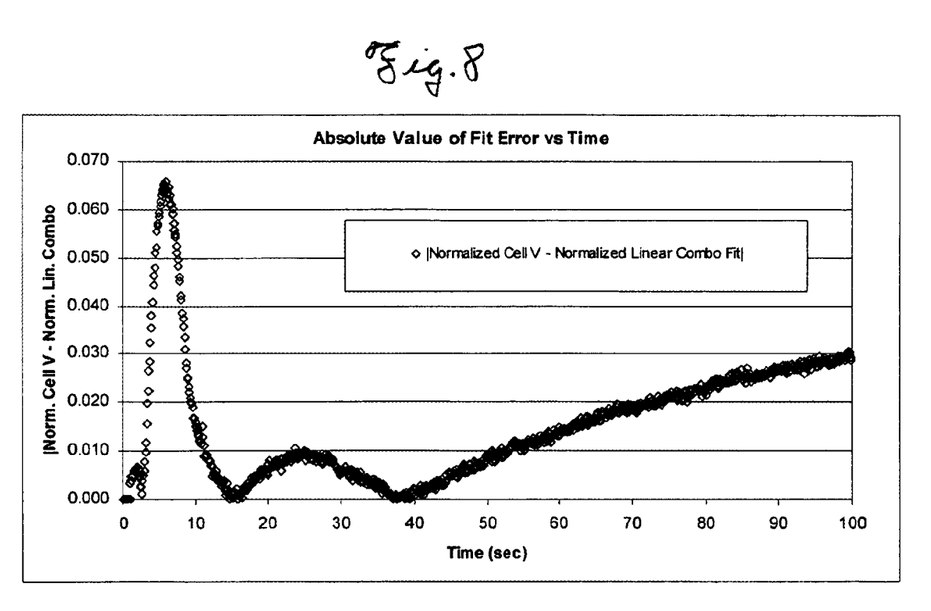
FIG. 8 is a plot of the absolute value of the second unknown sample response minus the normalized recombination fit for the data in FIG. 7.

Results from a first sample are shown in FIG. 5. The curve was de-convoluted to obtain the contributions from the cigarette smoke and the ethanol, with the ethanol contribution having a larger magnitude and reaching a peak maximum at a significantly later time. A curve is also plotted of the ethanol and cigarette smoke linearly recombined. The linearly recombined curve is very close to the curve of an unknown sample. FIG. 6 is a graph of the absolute value of the normalized response to the unknown sample minus the normalized linear combination fit for the data depicted in FIG. 5. The sum of these errors yields the total gross error, which in this example, is 3.798. The time dependent response of the fuel cell from a second sample is shown in FIG. 7 along with the de-convoluted ethanol and cigarette smoke responses and the linear fit curve. FIG. 8 is a graph of the absolute value of the normalized response to the unknown sample minus the normalized linear combination fit for the data depicted in FIG. 7. In this example, the gross error is 15.316. These are acceptable errors for this analysis.

This example illustrates that the fuel cell test device can be used to identify multiple organic components in a sample. Additionally, the data presented below in Table 1 represents results from 10 typical samples. The results were produced using the fuel cell device described above. The results in Table 1 indicate that the fuel cell test devices, along with the equations described above, can accurately determine the BrAC of an individual who is consuming alcohol and smoking cigarettes. Thus, the fuel cell test devices can accurately determine the presence and relative amounts of multiple organic compounds in a sample. The coefficient C in Table 1 is another notation for the parameter A from Eq. 3 for these particular analytzes.

TABLE 1

| # Clean Breaths After Cigarette | Ethanol Consumed | C | BrAC From Fit | GE |
|---|---|---|---|---|
| Person X (Male) | | | | |
| 0 | 2 oz. in ~43 min. | 0.117 | 0.05 | 12.564 |
| 1 | 2.5 oz. in ~57 min | 0.299 | 0.06 | 6.022 |
| 2 | 3 oz. in ~73 min | 0.468 | 0.06 | 3.831 |
| 4 | 3 oz. in ~96 min | 0.632 | 0.07 | 5.771 |
| >100 (~10 min after last draw) | 3 oz. in ~165 min | 0.641 | 0.06 | 8.141 |
| Person Y (Female) | | | | |
| 0 | 1.5 oz. in ~29 min | 0.130 | 0.05 | 10.063 |
| 1 | 2 oz. in ~48 min | 0.543 | 0.08 | 5.684 |
| 2 | 2.5 oz. in ~61 min | 0.637 | 0.08 | 15.316 |
| 4 | 3 oz. in ~92 min | 0.683 | 0.08 | 8.798 |
| >300 (~30 min after last draw) | 3 oz. in ~160 min | 0.770 | 0.08 | 11.290 |

What is claimed is:

1. A system comprising:
a sample collector;
a flow apparatus that is configured to receive a sample from the sample collector;
a fuel cell comprising an anode connected to the flow system apparatus wherein the sample transported within the flow system apparatus contacts the anode; and
an analyzer that receives a signal related to a signal from the fuel cell, and evaluates the amounts of a plurality of volatile organic compositions from the time response of the fuel cell signal as a function of time from a deconvolution of the time response of the fuel cell based on separate standard time response functions from each of the volatile organic compositions,
wherein the fuel cell comprises an electrolyte comprising a perfluoronated, sulfonic acid polymer,
wherein the anode comprises a plurality of particles comprising platinum and carbon, and
wherein the anode comprises a porous, conductive carbon cloth gas diffusion layer.

2. The system of claim 1 wherein the sample collector comprises a mouthpiece.

3. The system of claim 1 wherein the flow system apparatus comprises a pump that facilitates control of the flow through the flow apparatus.

4. The system of claim 1 wherein the fuel cell comprises an ionomer as the electrolyte.

5. The system of claim 1 wherein the analyzer comprises a microprocessor.

6. The system of claim 1 wherein the analyzer performs a linear fit of the standard curves to approximate the sample time response.

7. The system of claim 1 wherein one of the volatile organic compositions is ethanol and another of the volatile organic compositions is a component of tobacco smoke.

8. The system of claim 1 wherein the system is a portable unit.

9. The system of claim 1 wherein the system further comprises an interface to a vehicle ignition system and wherein the analyzer prevents ignition of the vehicle engine if a volatile organic composition is measured above a selected value.

* * * * *